United States Patent
Eom et al.

(10) Patent No.: US 12,186,218 B2
(45) Date of Patent: Jan. 7, 2025

(54) COMPRESSION GARMENT FOR CORRECTING LOWER BODY SHAPE AND WALKING GAIT FOR ANGULAR DEFORMITY OF LEGS

(71) Applicant: DODREAMCREATIVE CO., LTD., Seoul (KR)

(72) Inventors: Tae Ho Eom, Seoul (KR); Seung Ah Lee, Seoul (KR)

(73) Assignee: DODREAMCREATIVE CO., LTD. (KR)

( * ) Notice: Subject to any disclaimer, the term of this patent is extended or adjusted under 35 U.S.C. 154(b) by 581 days.

(21) Appl. No.: 17/597,905

(22) PCT Filed: Sep. 10, 2019

(86) PCT No.: PCT/KR2019/011679
§ 371 (c)(1),
(2) Date: Jan. 28, 2022

(87) PCT Pub. No.: WO2021/020641
PCT Pub. Date: Feb. 4, 2021

(65) Prior Publication Data
US 2022/0241100 A1    Aug. 4, 2022

(30) Foreign Application Priority Data

Jul. 29, 2019 (KR) .................. 10-2019-0091646

(51) Int. Cl.
*A61F 5/01* (2006.01)
*A41D 1/00* (2018.01)
*A41D 1/06* (2006.01)

(52) U.S. Cl.
CPC ............ *A61F 5/0109* (2013.01); *A41D 1/007* (2013.01); *A41D 1/067* (2013.01); *A41D 2400/32* (2013.01)

(58) Field of Classification Search
CPC .......... A41D 1/007; A41D 1/06; A41D 1/067; A41D 2400/32; A41D 2400/38;
(Continued)

(56) References Cited

U.S. PATENT DOCUMENTS

| 6,142,965 A | 11/2000 | Mathewson |
| 2012/0100778 A1* | 4/2012 | Cho ........................ A41D 1/06 450/95 |

FOREIGN PATENT DOCUMENTS

| CN | 102421309 A | 4/2012 |
| CN | 204483146 U | 7/2015 |
| CN | 208640993 U | 3/2019 |
| CN | 109864842 A | 6/2019 |

(Continued)

*Primary Examiner* — Alireza Nia
*Assistant Examiner* — Daniel A Miller
(74) *Attorney, Agent, or Firm* — Stetina Brunda Garred & Brucker (57) ABSTRACT

A compression garment for correcting a lower body shape and a walking gait for an angular deformity of the legs, according to the present embodiment, comprises: a bottom garment main body; and a correction band disposed on the bottom garment main body, wherein the correction band includes a first correction band disposed in a first area of the bottom garment main body and a second correction band disposed in a second area of the bottom garment main body, the first correction band composed of a first part disposed above the first area, a second part disposed below the first area, and a third part connecting the first part of the first correction band and the second part of the first correction band, and the second correction band composed of a first part disposed above the second area, a second part disposed below the second area, and a third part connecting the first part of the second correction band and the second part of the second correction band. The first correction band comprises a connecting member disposed on the first part of the first correction band and including a hole, and the first part of the second correction band may be inserted into the hole of the (Continued)

connecting member of the first correction band and coupled by means of a belt fastening method.

11 Claims, 6 Drawing Sheets

(58) Field of Classification Search
CPC .... A41D 2400/82; A41D 13/00; A41D 13/02; A41D 13/0015; A41D 13/0012; A61F 5/0109; A61F 5/0104; A61F 5/0106; A61F 5/03; A61F 5/0123; A61F 5/30; A61F 5/0125; A61F 5/02; A61F 5/0102; A61F 5/012
USPC .......................................................... 602/26
See application file for complete search history.

(56) References Cited

FOREIGN PATENT DOCUMENTS

| | | | |
|---|---|---|---|
| JP | 2002-514105 | A | 5/2002 |
| JP | 2002-253701 | A | 9/2002 |
| JP | 2004238789 | A | 8/2004 |
| JP | 2005160982 | A | 6/2005 |
| JP | 2012-526602 | A | 11/2012 |
| JP | 2015016195 | A | 1/2015 |
| JP | 2017047151 | A | 3/2017 |
| JP | 6278436 | B2 | 2/2018 |
| KR | 10-1064031 | B1 | 9/2011 |
| KR | 20130003370 | U | 6/2013 |
| KR | 10-1467143 | B1 | 12/2014 |
| KR | 101500297 | B1 | 3/2015 |
| KR | 10-2015-0095315 | A | 8/2015 |
| KR | 10-2019-0046088 | A | 5/2019 |

* cited by examiner

FIG. 9

COMPRESSION GARMENT FOR CORRECTING LOWER BODY SHAPE AND WALKING GAIT FOR ANGULAR DEFORMITY OF LEGS

CROSS-REFERENCE TO RELATED APPLICATIONS

This application claims priority to PCT International Application No. PCT/KR2019/011679 filed on Sep. 10, 2019, which application claims priority to Korean Patent Application No. 10-2019-0091646 filed on Jul. 29, 2019, the entire disclosures of which are expressly incorporated herein by reference.

STATEMENT RE: FEDERALLY SPONSORED RESEARCH/DEVELOPMENT

Not Applicable

BACKGROUND

Technical Field

This embodiment relates to a compression garment for correcting lower body shape and walking gait for angular deformity of legs.

Background Art

For a normal leg, the femur and tibia should form an ideal angle, and the left and right knee joints should be balanced, but the hip joint and knee joint are misaligned due to congenital causes or acquired lifestyle or posture, resulting in a bow leg such as an O-shaped leg or an X-shaped leg.

The bow leg is not good to look at, and there is a problem that the outer gap of the knee joint widens and the friction of the inner cartilage of the knee increases, which leads to the development of degenerative arthritis. Therefore, correcting the bent legs is a subject of much interest in terms of beauty and health.

For the bow leg, there are surgical methods such as corrective surgery and methods using an orthotast or retainer. However, in the case of corrective surgery, orthotast or retainer, the effect of correcting the bow leg is immediate, but there is a problem with high cost and large side effects. As a simpler method, there is a method using a belt for tying the legs. However, the belt simply compresses the knee inward, and there is a problem that the effect of correction is insignificant.

BRIEF SUMMARY

Technical Subject

The present embodiment is proposed to improve the above problems, and it is to provide a compression garment for correcting lower body shape and walking gait for angular deformity of legs, in which the leg is firstly pressed using taping members with different densities, and the leg is secondarily pressed using a correction band made of an inelastic material, thereby being able to correct bow leg and pelvis.

In addition, it is possible to induce correction with the correct walking gait method by holding the user's pelvis and knee joints to maintain a normal angle while walking through the correction band.

In addition, by dispersing the weight applied to the lower part of the user through the correction band, it is possible to induce correction with the correct walking gait method.

Technical Solution

A compression garment for correcting a lower body shape and a walking gait for an angular deformity of the legs, according to the present embodiment, comprises: a bottom garment main body; and a correction band disposed on the bottom, wherein the correction band includes a first correction band disposed in a first area of the bottom garment main body and a second correction band disposed in a second area of the bottom garment main body, wherein the first correction band includes a first part disposed above the first area, a second part disposed below the first area, and a third part connecting the first part of the first correction band and the second part of the first correction band, wherein the second correction band includes a first part disposed above the second area, a second part disposed below the second area, and a third part connecting the first part of the second correction band and the second part of the second correction band, wherein the first correction band includes a connecting member disposed on the first part of the first correction band and including a hole, and wherein the first part of the second correction band may be inserted into the hole of the connecting member of the first correction band and coupled by means of a belt fastening method.

In addition, the first part and the third part of the first correction band and the first part and the third part of the second correction band are formed of an inelastic material, and the second part of the first correction band and the second part of the second correction band may be formed of an elastic material.

In addition, the third part of the first correction band includes a bent portion formed in a portion being connected from the front side of the first area of the bottom garment main body to the rear side thereof, and the third part of the second correction band may include a bent portion being formed in a portion being connected from a front side of the second area of the bottom garment main body to a rear side thereof.

In addition, the first area of the bottom garment main body includes a ring formed at a position corresponding to the bent portion of the third part of the first correction band, and the second area of the bottom garment main body may include a ring formed at a position corresponding to the bent portion of the third part of the second correction band.

In addition, the bent portion of the third part of the first correction band includes a first bent portion disposed on an outer side surface of the first area of the bottom garment main body, and a second bent portion spaced apart from the first bent portion and disposed on an inner side surface of the first area of the bottom garment main body; and the bent portion of the third part of the second correction band may include a third bent portion disposed on an outer side surface of the second area of the bottom garment main body, and a fourth bent portion spaced apart from the third bent portion and disposed on an inner side surface of the second area of the bottom garment main body.

In addition, the first bent portion of the third part of the first correction band is disposed closer to the second part of the first correction band than the first part of the first correction band; the second bent portion of the third part of the first correction band is disposed closer to the first part of the first correction band than the second part of the first correction band; the third bent portion of the third part of the second correction band is disposed closer to the second part of the second correction band than the first part of the second correction band; and the fourth bent portion of the third part of the second correction band may be disposed closer to the first part of the second correction band than the second part of the first correction band.

In addition, the first area of the bottom garment main body includes first and second rings formed at positions corresponding to the first and second bent portions of the first correction band and including holes; the second area of the bottom garment main body includes third and fourth rings formed at positions corresponding to the third and fourth bent portions of the second correction band and including holes; each of the first and second bent portions of the first correction band is respectively inserted into the first and second rings of the first area of the bottom garment main body; and each of the third and fourth bent portions of the second correction band may be respectively inserted into the third and fourth rings of the second area of the bottom garment main body.

In addition, the first to fourth rings may be detachable from and attachable to the bottom garment main body.

In addition, the bottom garment main body includes: a first taping member continuously wound in a first direction from an upper portion of the first area to a lower portion of the first area; and a second taping member continuously wound in a second direction from an upper portion of the first area to a lower portion of the first area, wherein the first direction and the second direction may be opposite directions.

In addition, a density of the first taping member may be different from a density of the second taping member.

In addition, the density of the first taping member may be greater than the density of the second taping member.

In addition, the correction band may be detachable from and attachable to the bottom garment main body.

Advantageous Effects

Through the present embodiment, it is possible to correct the lower body shape such as bow legs and pelvic deformity.

In addition, angle correction of the pelvis and knee joints is possible.

In addition, the position of the correction band can be adjusted according to the user's characteristics.

In addition, incorrect walking gait such as nasolabial gait can be corrected correctly.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 1 (a) is a drawing illustrating the front of a bottom garment main body of a compression garment for correcting lower body shape and walking gait for angular deformity of legs according to the present embodiment, and FIG. 1 (b) is a drawing illustrating a rear side of the bottom garment main body of a compression garment for correcting lower body shape and walking gait for angular deformity of legs according to the present embodiment.

DETAILED DESCRIPTION

Hereinafter, preferred embodiments of the present invention will be described in detail with reference to the accompanying drawings.

However, the technical idea of the present invention is not limited to some embodiments to be described, but may be implemented in various forms, and within the scope of the technical idea of the present invention, one or more of the constituent elements may be selectively combined or substituted between embodiments.

In addition, the terms (including technical and scientific terms) used in the embodiments of the present invention, unless explicitly defined and described, can be interpreted as a meaning that can be generally understood by a person skilled in the art, and commonly used terms such as terms defined in the dictionary may be interpreted in consideration of the meaning of the context of the related technology.

In addition, terms used in the present specification are for describing embodiments and are not intended to limit the present invention.

In the present specification, the singular form may include the plural form unless specifically stated in the phrase, and when described as "at least one (or more than one) of A and B and C", it may include one or more of all combinations that can be combined with A, B, and C.

In addition, in describing the components of the embodiment of the present invention, terms such as first, second, A, B, (a), and (b) may be used. These terms are merely intended to distinguish the components from other components, and the terms do not limit the nature, order or sequence of the components.

And, when a component is described as being 'connected', 'coupled' or 'interconnected' to another component, the component is not only directly connected, coupled or interconnected to the other component, but may also include cases of being 'connected', 'coupled', or 'interconnected' due that another component between that other components.

In addition, when described as being formed or arranged in "on (above)" or "below (under)" of each component, "on (above)" or "below (under)" means that it includes not only the case where the two components are directly in contact with, but also the case where one or more other components are formed or arranged between the two components. In addition, when expressed as "on (above)" or "below (under)", the meaning of not only an upward direction but also a downward direction based on one component may be included.

Hereinafter, a preferred embodiment of the compression garment for correcting lower body shape and walking gait for angular deformity of legs according to the present embodiment will be described in detail with reference to the accompanying drawings.

Figure 1:
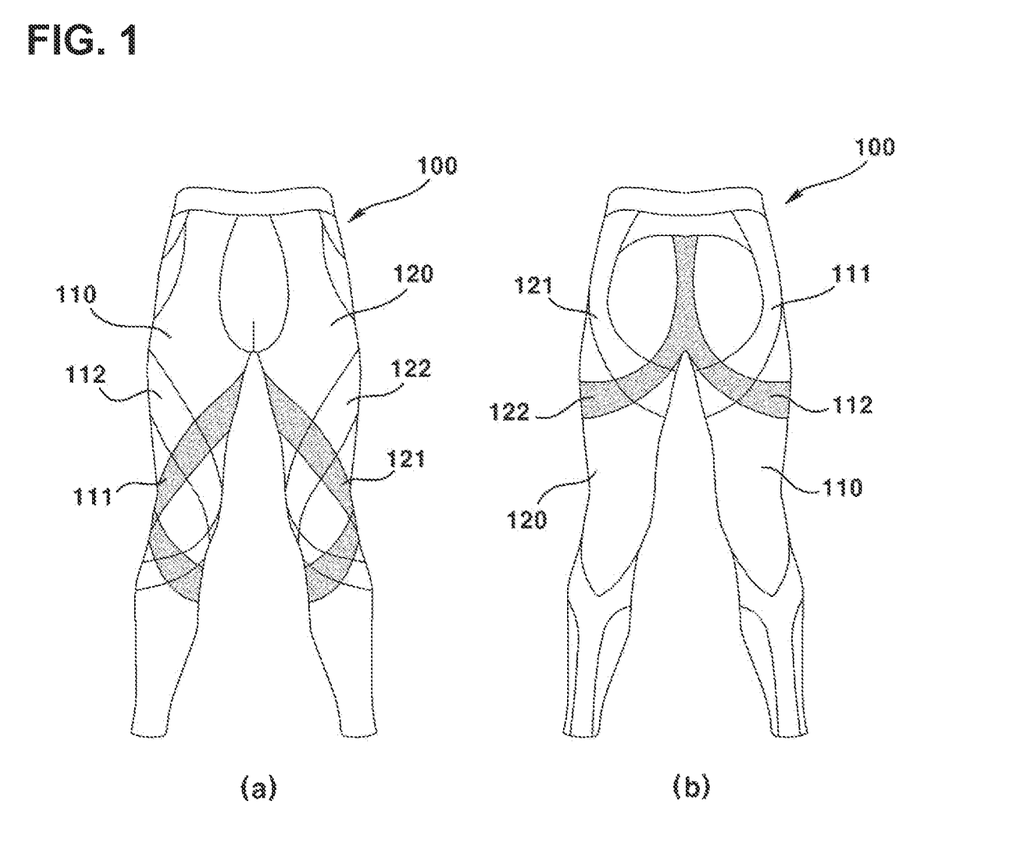
Figure 2:
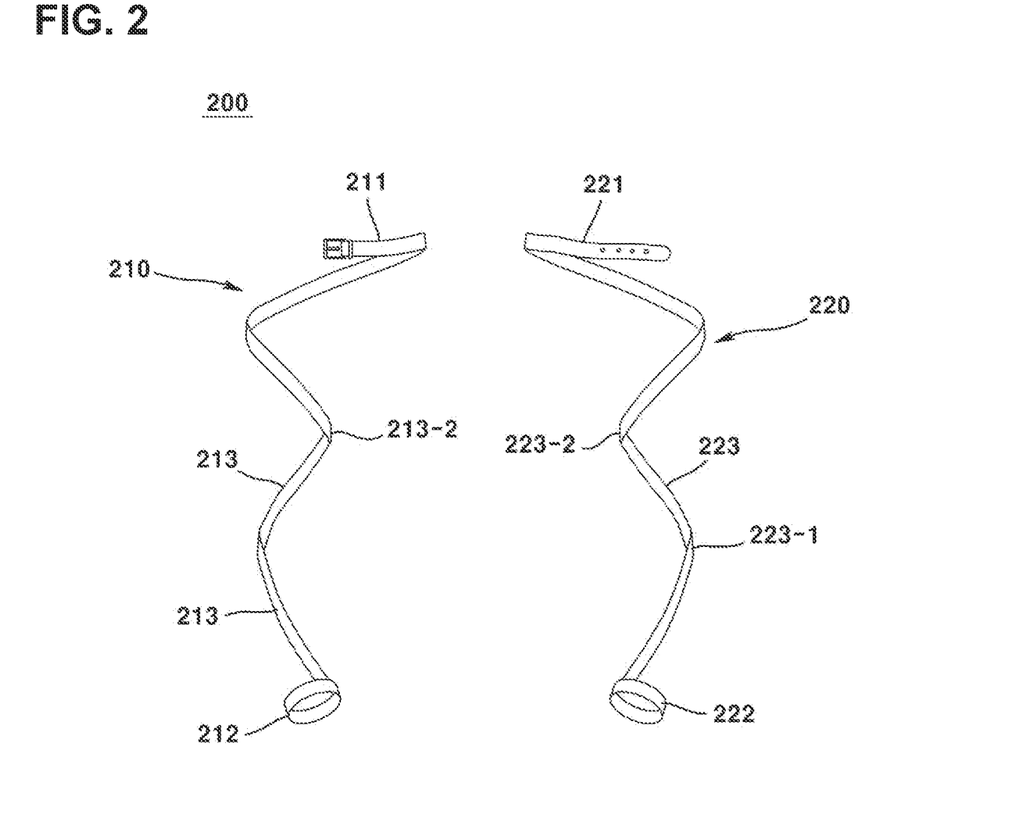
FIG. 2 is a drawing illustrating a correction band of a compression garment for correcting lower body shape and walking gait for angular deformity of legs according to the present embodiment.
Figure 3:
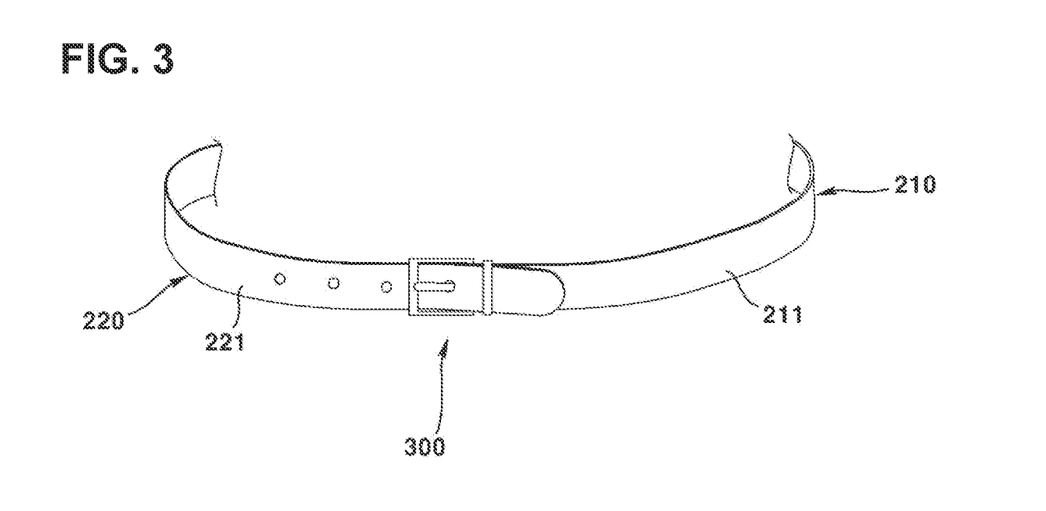
FIGS. 3 to 5 are diagrams illustrating a partial configuration of the correction band of a compression garment for correcting lower body shape and walking gait for angular deformity of legs according to the present embodiment.
Figure 4:
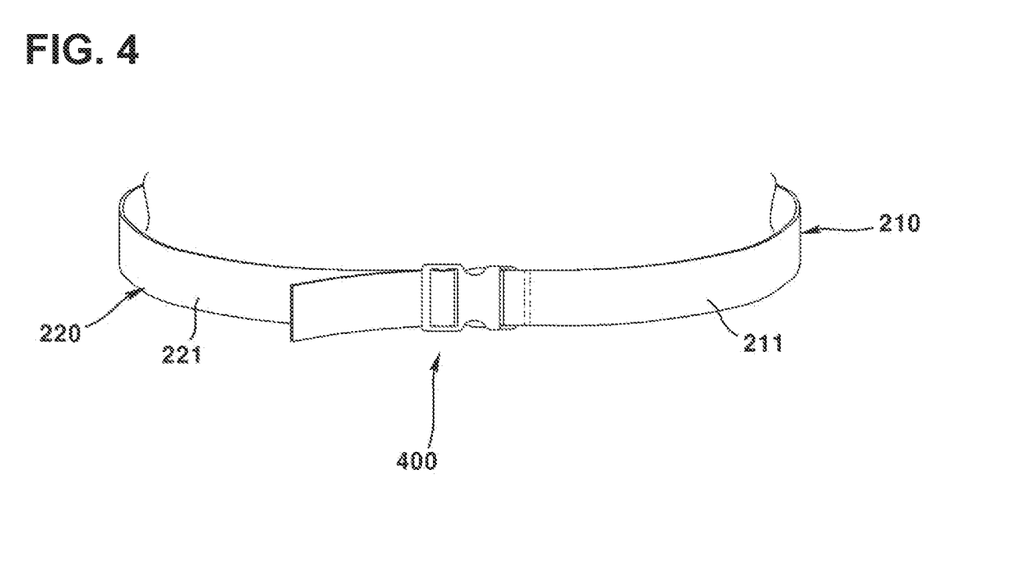
Figure 5:
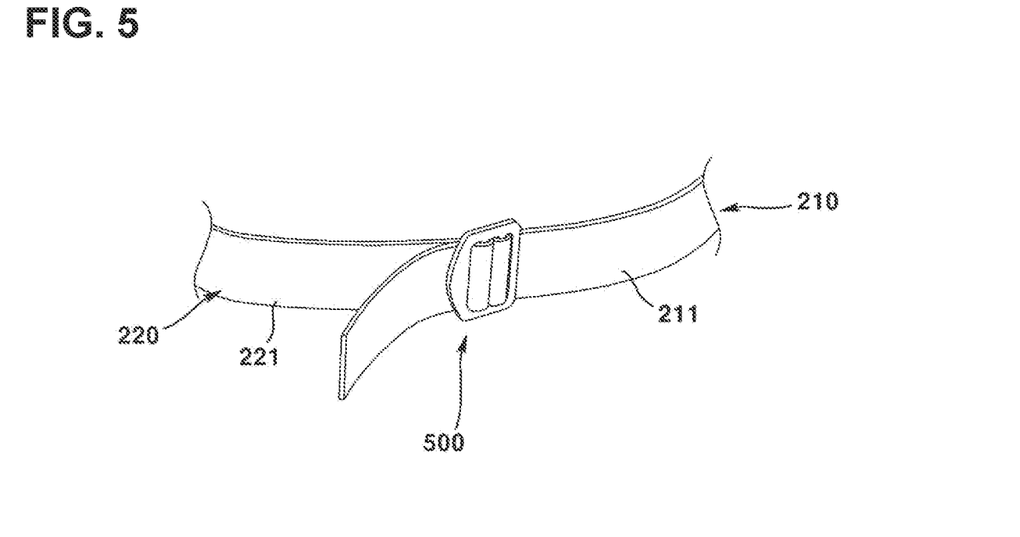
Figure 6:
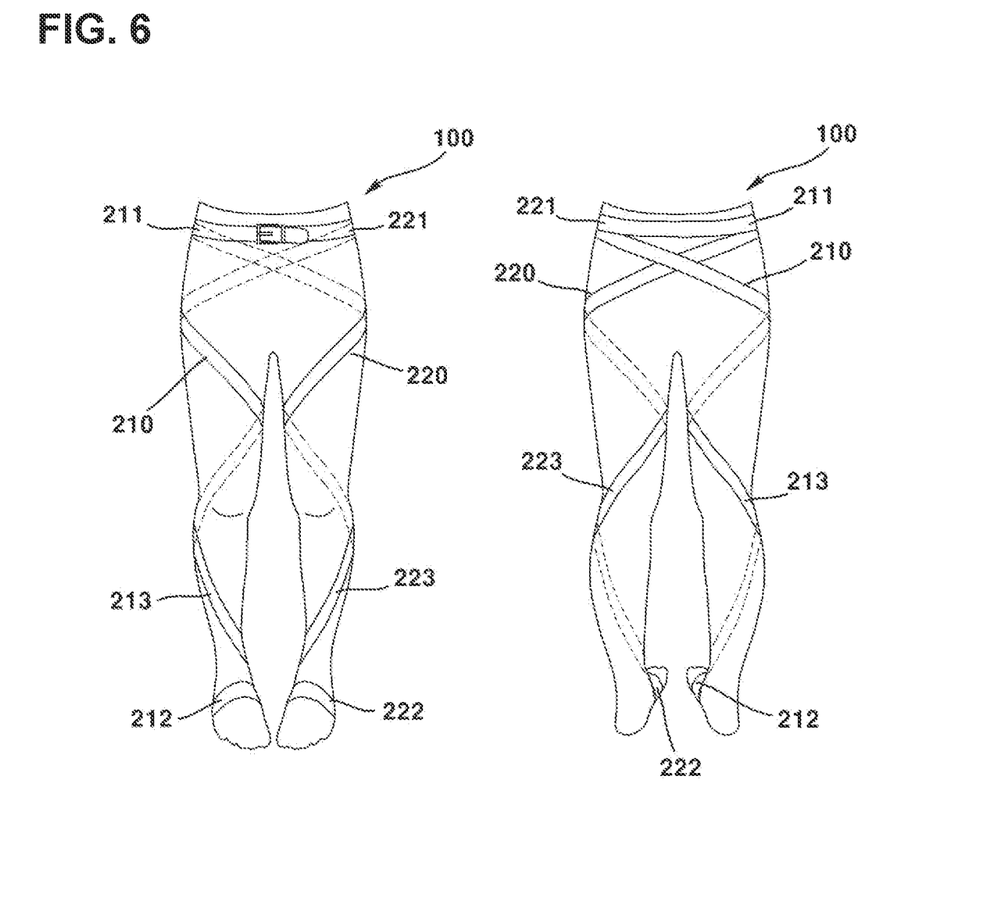
FIG. 6 is a drawing illustrating an assembly view of the bottom garment main body and correction band of a compression garment for correcting lower body shape and walking gait for angular deformity of legs according to the present embodiment.
Figure 7:
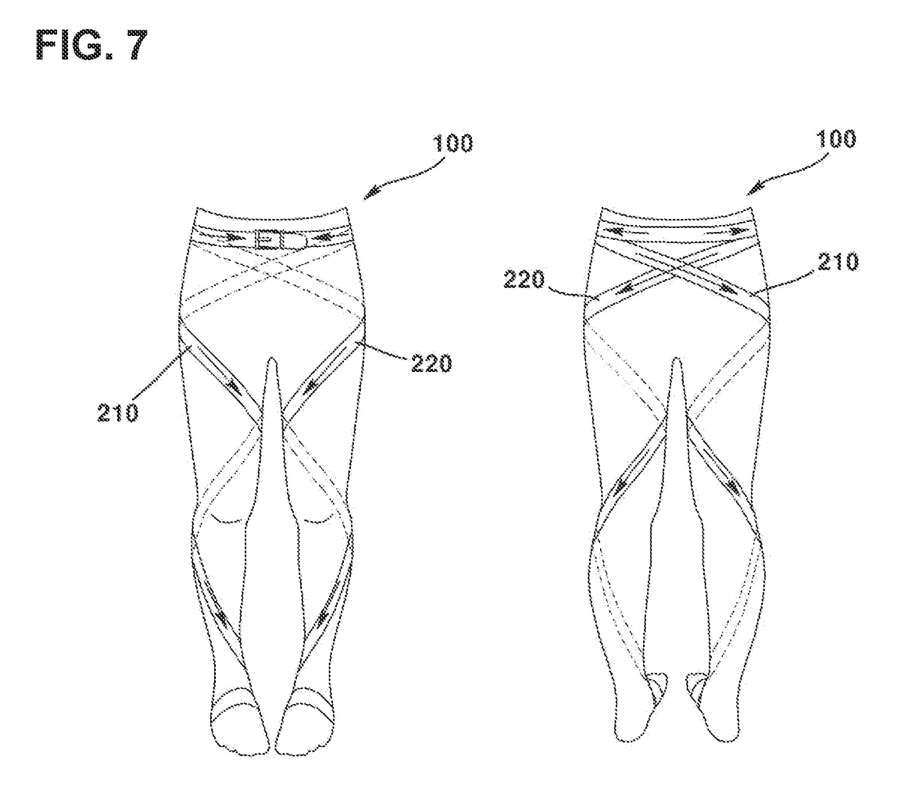
FIG. 7 is a drawing illustrating a direction corrected by a correction band of a compression garment for correcting lower body shape and walking gait for angular deformity of legs according to the present embodiment.
Figure 8:
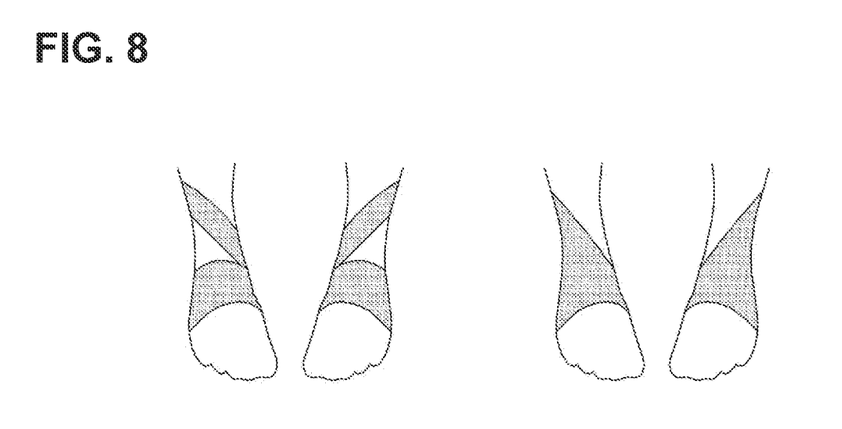
FIG. 8 is a drawing illustrating a partial configuration of a correction band of a compression garment for correcting lower body shape and walking gait for angular deformity of legs according to the present embodiment.
Figure 9:
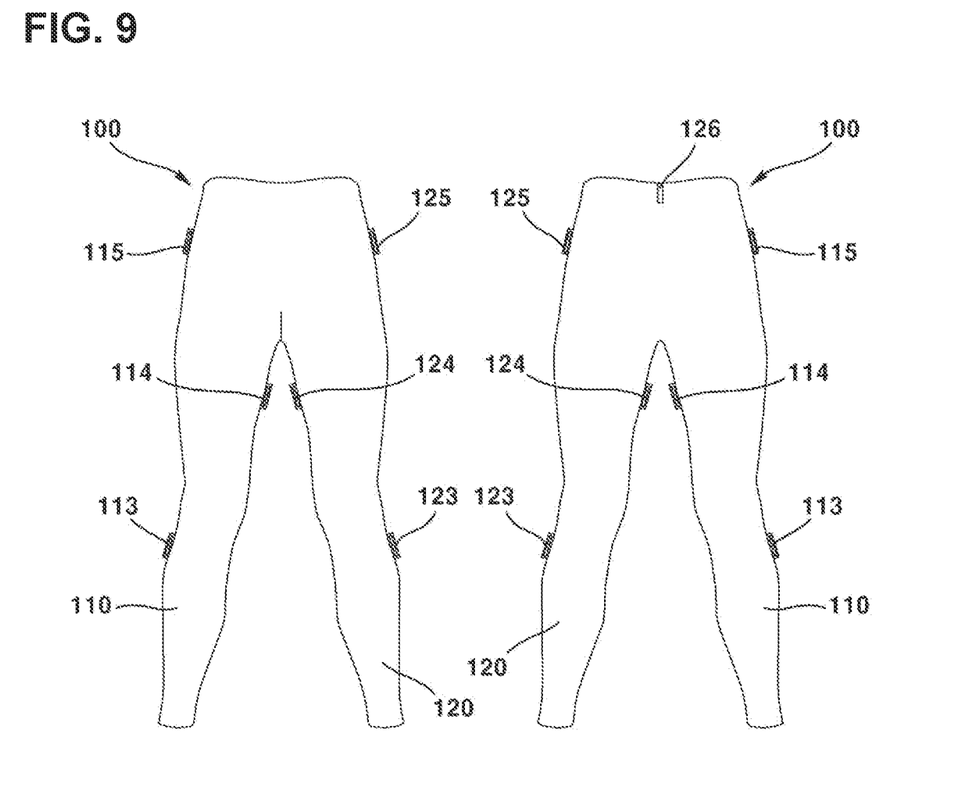
FIG. 9 is a drawing illustrating rings of a bottom garment main body of a compression garment for correcting lower body shape and walking gait for angular deformity of legs according to the present embodiment.

FIG. 1 (*a*) is a drawing illustrating the front of a bottom garment main body of a compression garment for correcting lower body shape and walking gait for angular deformity of legs according to the present embodiment, and FIG. 1 (*b*) is a drawing illustrating a rear side of the bottom garment main body of a compression garment for correcting lower body shape and walking gait for angular deformity of legs according to the present embodiment. FIG. 2 is a drawing illustrating a correction band of a compression garment for correcting lower body shape and walking gait for angular deformity of legs according to the present embodiment. FIGS. 3 to 5 are diagrams illustrating a partial configuration of the correction band of a compression garment for correcting lower body shape and walking gait for angular deformity of legs according to the present embodiment. FIG. 6 is a drawing illustrating an assembly view of the bottom garment main body and correction band of a compression garment for correcting lower body shape and walking gait for angular deformity of legs according to the present embodiment. FIG. 7 is a drawing illustrating a direction corrected by a correction band of a compression garment for correcting lower body shape and walking gait for angular deformity of legs according to the present embodiment.

The compression garment for correcting lower body shape and walking gait for angular deformity of legs according to the present embodiment may be for correcting O-legs. The compression garment for correcting lower body shape and walking gait for angular deformity of legs may be for correcting bow legs. A compression garment for correcting lower body shape and walking gait for angular deformity of legs may be for correcting X-shaped legs. A compression garment for correcting lower body shape and walking gait for angular deformity of legs may be for walking gait correction. Specifically, it may be for inducing an incorrect walking gait such as a nasolabial gait to a straight walking gait. However, the present invention is not limited thereto and may be used for angle correction of rotational deformation of the knee joint, deformation of the pelvis, rotational deformation of the ankle, or the like.

The compression garment for correcting lower body shape and walking gait for angular deformity of legs according to the present embodiment may include a bottom garment main body 100. The bottom garment main body 100 may be formed in the form of pants worn on the user's lower body. The bottom garment main body 100 may be formed in the form of long pants or shorts. The upper part of the bottom garment main body 100 may include a waist portion that is placed on the user's waist. The bottom garment main body 100 may include a calf portion that is placed on the user's calf. The lower part of the bottom garment main body 100 may include an ankle portion disposed on the user's ankle. The bottom garment main body 100 may be extended from the upper part to the lower part.

The bottom garment main body 100 may include a first area 110 disposed on the left side and a second area 120 disposed on the right side based on (a) of FIG. 1. It may be extended from the top to the bottom of the first area 110. The second area 120 may be extended from the upper part to the lower part.

The compression garment for correcting lower body shape and walking gait for angular deformity of legs according to the present embodiment may include a first taping member 111. The first taping member 111 may be disposed in the first area 110 of the bottom garment main body 100. The first taping member 111 may be continuously wound from the upper part of the bottom garment main body 100 to the lower part of the first area 110. At this time, the first taping member 111 may be rotated in a first direction. In addition, the first taping member 111 may be rotated spirally. The first taping member 111 may be rotated and wound around the bottom garment main body 100 at least twice.

The density of the first taping member 111 may be different from the density of the bottom garment main body 100. Specifically, the density of the first taping member 111 may be greater than the density of the bottom garment main body 100. In this case, it may be possible to correct bow legs due to the pressure difference according to the difference in density of the fabric constituting the bottom garment main body 100 and the first taping member 111.

The compression garment for correcting lower body shape and walking gait for angular deformity of legs according to the present embodiment may include a second taping member 112. The second taping member 112 may be disposed in a first area 110 of the bottom garment main body 100. A portion of the second taping member 112 may be spaced apart from the first taping member 111. At least a portion of the second taping member 112 may be overlapped with the first taping member 111. The second taping member 112 may be wound continuously from the upper part to the lower part of the bottom garment main body 100. The second taping member 112 may be rotated and wound around the bottom garment main body 100 at least twice or more. In this case, the second taping member 112 may be rotated in a second direction. In addition, the second taping member 112 may be rotated in a spiral manner. The first direction may be opposite to the second direction. Specifically, when the first direction is a clockwise direction, the second direction may be a counterclockwise direction. When the first direction is a counterclockwise direction, the second direction may be a clockwise direction.

The compression garment for correcting lower body shape and walking gait for angular deformity of legs according to the present embodiment may include a third taping member 121. The third taping member 121 may be disposed in the second area 120 of the bottom garment main body 100. The third taping member 121 may be continuously wound from the upper part of the bottom garment main body 100 to the lower part of the second area 120. In this case, the third taping member 121 may be rotated in a third direction. In addition, the third taping member 121 may be rotated in a spiral manner. The third taping member 121 may be rotated and wound around the bottom garment main body 100 at least twice or more.

The density of the third taping member 121 may be different from the density of the bottom garment main body 100. Specifically, the density of the third taping member 121 may be greater than the density of the bottom garment main body 100. In this case, it may be possible to correct bow legs due to the pressure difference according to the difference in density of the fabric constituting the bottom garment main body 100 and the third taping member 121.

The compression garment for correcting lower body shape and walking gait for angular deformity of legs according to the present embodiment may include a fourth taping member 122. The fourth taping member 122 may be disposed in a second area 120 of the bottom garment main body 100. A portion of the fourth taping member 122 may be spaced apart from the third taping member 121. At least a portion of the fourth taping member 122 may be overlapped with the third taping member 121. The fourth taping member 122 may be continuously wound from the upper part to the lower part of the bottom garment main body 100. The fourth taping member 122 may be rotated and wound around the bottom garment main body 100 at least twice or more. At this time, the fourth taping member 122 may be rotated in a fourth direction. In addition, the fourth taping member 122 may be helically rotated. The third direction may be opposite to the fourth direction. Specifically, when the third direction is a clockwise direction, the fourth direction may be a counterclockwise direction. When the third direction is a counterclockwise direction, the fourth direction may be a clockwise direction.

The first direction and the third direction may be the same direction. The second direction and the fourth direction may be the same direction. However, it is not limited thereto, and each of the first to fourth directions may be appropriately adjusted according to the body type to be corrected.

The density of the second taping member 112 may be different from the density of the bottom garment main body 100. Specifically, the density of the second taping member 112 may be greater than the density of the bottom garment main body 100. In this case, bow legs can be corrected due to the pressure difference owing to the difference in the densities of the fabric constituting the bottom garment main body 100 and the second taping member 112.

The density of the first taping member 111 may be different from that of the second taping member 112. The density of the first taping member 111 may be greater than that of the second taping member 112. In this case, due to the pressure difference between the first taping member 111 and the second taping member 112, it may be possible to correct bow legs. Specifically, referring to FIG. 1, bow legs can be corrected by the force being pushed from the outer side to the inner side by the first taping member 111 disposed on an outer side near the knee joint.

The density of the first taping member 111 may be less than that of the second taping member 112. In this case, the X-shaped leg correction may be possible due to a pressure difference between the first taping member 111 and the second taping member 112. Specifically, referring to FIG. 1, the X-shaped leg can be corrected by the force being pushed from the inner side to the outer side by the second taping member 112 disposed on an inner side near the knee joint.

The density of the third taping member 121 may be different from that of the fourth taping member 122. The density of the third taping member 121 may be greater than that of the fourth taping member 122. In this case, due to the pressure difference between the third taping member 121 and the fourth taping member 122, it may be possible to correct bow legs. Specifically, referring to FIG. 1, bow legs can be corrected by the force being pushed from the outer side to the inner side by the third taping member 121 disposed on the outer side near the knee joint of the second area 120 of the bottom garment main body 100.

The density of the third taping member 121 may be less than that of the fourth taping member 122. In this case, X-shaped legs can be corrected due to a pressure difference between the third taping member 121 and the fourth taping member 122. Specifically, referring to FIG. 1, X-shaped legs can be corrected by the force being pushed from the inner side to the outer side by the third taping member 121 disposed on the inner side of the knee joint of the second area 120 of the bottom garment main body 100.

The first taping member 111 and the third taping member 121 may have the same density, and the second taping member 112 and the fourth taping member 122 may have the same density. Through this, it may be possible to correct bow legs or X-shaped legs. However, it is not limited thereto, and the density of each of the first to fourth taping members 111, 112, 121, and 122 may be variously set according to a body shape to be corrected.

The compression garment for correcting lower body shape and walking gait for angular deformity of legs according to the present embodiment may include a correction band 200. The correction band 200 may be disposed on the bottom garment main body 100. The correction band 200 may be detachable from and attachable to the bottom garment main body 100. The correction band 200 may be disposed on the upper surfaces of the first to third taping members 111, 112, 121, and 122. The correction band 200 may be detachable from and attachable to the bottom garment main body 100. The correction band 200 may include a first correction band 210 disposed in the first area 110 of the bottom garment main body 100. The correction band 200 may include a second correction band 220 in which the bottom garment main body 100 is disposed in the second area 120.

The first correction band 210 may include a first part 211 disposed on the upper portion of the bottom garment main body 100. The second correction band 220 may include a second part 212 disposed in at least a portion of the lower portion of the first area 110 of the bottom garment main body 100. The first correction band 210 may include a third part 213 connecting the first part 211 and the second part 212 of the first correction band 210.

The second correction band 220 may include a first part 221 disposed on the upper portion of the bottom garment main body 100. The second correction band 220 may include a second part 222 disposed in at least a portion of the lower portion of the second area 120 of the bottom garment main body 100. The second correction band 220 may include a third part 223 connecting the first part 221 and the second part 222 of the second correction band 220.

The first correction band 210 and the second correction band 220 may be combined by a belt fastening method. The first part 211 of the first correction band 210 may include a connecting member 300. The connecting member 300 may include a hole. Specifically, the connecting member 300 may include a buckle, a hole, and a pin. Referring to FIG. 3, the second part 221 of the second correction band 220 is inserted into the hole of the connecting member 300 of the first part 211 of the first correction band 210 and may be fixed by the belt fastening method. In this case, a plurality of holes may be formed in the first part 221 of the second correction band 220. Through this, the correction band 200 can adjust the size according to the user's body type. In addition, it is possible to tighten the belt strongly or weakly, so that the strength of the correction can be adjusted according to the degree of bending of the leg.

In addition, the first correction band 210 and the second correction band 220 may be fixed with a Velcro tape in addition to the belt fastening method. A first Velcro tape (not shown) may be disposed on the first part 211 of the first correction band 210, and a second Velcro tape (not shown) may be disposed on the first part 221 of the second correction band 220. The correction band 200 may be fixed by the first and second Velcro tapes. In addition, the horizontal lengths of the first and second Velcro tapes may be extended along the first parts 211 and 221 of the first and second correction bands 210 and 220 so that the correction band 200 can be fixed according to the user's body size.

In addition, the first correction band 210 and the second correction band 220 may be fixed in a strap type other than the belt fastening method. Specifically, the correction band 200 may be fixed by bundling the first part 211 of the first correction band 210 and the first part 221 of the second correction band 220. In this case, no fixing member is required, and the size may be adjusted according to the user's body. In addition, correction efficiency can be increased by adjusting the bundling position or strength according to the degree of correction required.

In addition, the first correction band 210 and the second correction band 220 may be fixed in a hook type other than the belt fastening method. For example, a hook (not shown) may be disposed on the first part 211 of the first correction band 210, and a hook (not shown) may be disposed on the first part 221 of the second correction band 220. In this case, the correction band 200 may be fixed as the hook is caught in the ring.

In addition, the first correction band 210 and the second correction band 220 may be fixed through the fastening member 400 in addition to the belt fastening method. Specifically, the first fastening member may be disposed on the first part 211 of the first correction band 210, and the second fastening member may be disposed on the first part 221 of the second correction band 220. The second fastening member may be inserted into and fixed to the first fastening member.

In addition, the first correction band 210 and the second correction band 220 may be fixed through the length adjusting member 500 in addition to the belt fastening method. Specifically, the length adjusting member 500 may be disposed in the first part 211 of the first correction band 210. The length adjustment member 500 may include a first hole and a second hole that are spaced apart. The first part 221 of the second correction band 220 may pass through the first hole of the length adjusting member 500 and be inserted into the second hole to be fixed.

The first correction band 210 may include a bent portion. The bent portion may be formed in the third part 213 of the first correction band 210. The bent portion may be formed in a portion being connected from the front side of the first area 110 of the bottom garment main body 100 to the rear side thereof. The bent portion may be formed in a portion being connected from the rear side of the first area 110 of the bottom garment main body 100 to the front side thereof. The bent portion may include the first bent portion 213-1. The first bent portion 213-1 may be disposed on an outer side surface of the first area 110 of the bottom garment main body 100. The first bent portion 213-1 may be disposed on an outer side surface being connected from the front side of the first area 110 of the bottom garment main body 100 to the rear side thereof. The bent portion may include a second bent portion 213-2. The second bent portion 213-2 may be disposed on an inner side surface of the first area 110 of the bottom garment main body 100. The second bent portion 213-2 may be disposed on an inner surface being connected from the rear side of the first area 110 of the bottom garment main body 100 to the front side thereof.

The first bent portion 213-1 may be disposed closer to the second part 212 than the first part 211 of the first correction band 200. The second bent portion 213-2 may be disposed closer to the first part 111 than the second part 212 of the first correction band 210.

The first area 110 of the bottom garment main body 100 may include a ring formed at a position corresponding to the bent portion of the third part 213 of the first correction band 210. The first area 110 of the bottom garment main body 100 is formed at a position corresponding to the first and second bent portions 213-1 and 213-2 of the first correction band 210 and may include a first and a second rings 113 and 114 including holes therein respectively.

The third part 213 of the first correction band 210 may pass through the first ring 113. The first correction band 210 passing through the first ring 113 may be extended to the second ring 114 and pass through the second ring 114. Due to this, the first correction band 210 may generate a pressure applied in the direction from the outer side to the inner side of the user's leg. That is, due to the first correction band 210, it may be possible to correct bow legs. In addition, when using the first correction band 210 together with the first and second taping members 111 and 112 of the bottom garment main body 100, it is possible to strongly press from the outer side to the inner side of the user's leg, so that an effect in correction can be seen in a short time, and correction can be possible even in the case of severe bow legs.

The second correction band 220 may include a bent portion. The bent portion may be formed in the third part 223 of the second correction band 220. The bent portion may be formed in a portion being connected from the front side of the second area 120 of the bottom garment main body 100 to rear side thereof. The bent portion may be formed in a portion being connected from the rear side of the second area 120 of the bottom garment main body 100 to the front side thereof. The bent portion may include a third bent portion 223-1. The third bent portion 223-1 may be disposed on the outer side surface of the second area 120 of the bottom garment main body 100. The third bent portion 223-1 may be disposed on an outer surface being connected from the front side of the second area 120 of the bottom garment main body 100 to the rear side thereof. The bent portion may include a fourth bent portion 223-2. The fourth bent portion 223-2 may be disposed on an inner side surface of the second area 120 of the bottom garment main body 100. The fourth bent portion 223-2 may be disposed on an inner side surface being connected from the rear side of the second area 120 of the bottom garment main body 100 to the front side thereof.

The third bent portion 223-1 of the third part 223 of the second correction band 220 may be disposed closer to the second part 222 than the first part 221 of the second correction band 220. The fourth bent portion 223-2 of the third part 223 of the second correction band 220 may be disposed closer to the first part 221 than the second part 222 of the first correction band 210.

The second area 120 of the bottom garment main body 100 may include a third and a fourth rings 123 and 124 formed at a position corresponding to the third and fourth bent portions 223-1 and 223-2 of the second correction band 220 and including a hole. Each of the first and second bent portions 213-1 and 213-2 of the first correction band 210 can be respectively inserted into the first and second rings 113 and 114 of the first area 110 of the bottom garment main body 100. Each of the third and fourth bent portions 223-1 and 223-2 of the second correction band 220 can be respectively inserted into the third and fourth rings 123 and 124 of the second area 120 of the bottom garment main body 100.

The third part 223 of the second correction band 220 may pass through the third ring 123. The second correction band 220 passing through the third ring 123 may be extended to the fourth ring 124 and pass through the fourth ring 124. Due to this, the second correction band 220 may generate a pressure applied in the direction from the outer side to the inner side of the user's leg. That is, due to the second correction band 220, it may be possible to correct bow legs. In addition, when using the second correction band 220 together with the third and fourth taping members 121 and 122 of the bottom garment main body 100, it is possible to strongly press from the outer side to the inner side of the user's leg, so that an effect in correction can be seen in a short time, and correction can be possible even in the case of severe bow legs.

The bottom garment main body 100 may include a fifth hook 126 disposed on a rear side of an upper portion of the bottom garment main body 100. The first part 111 of the first correction band 210 and the first part 221 of the second correction band 220 may pass through the fifth ring 126. In this case, at least a portion of the first part 211 of the first correction band 210 may be overlapped with the first part 221 of the second correction band 220.

The bottom garment main body 100 may include sixth and seventh rings 115 and 125 disposed on an outer side surface of an upper portion of the bottom garment main body 100. A first correction band 210 being extended from the second bent portion 213-2 passes through the sixth ring 115 and may be inserted into the fifth ring 126 of the rear side of the bottom garment main body 100. A second correction band 220 being extended from the fourth bent portion 223-2 passes through the seventh ring 125 and may be inserted into the fifth ring 126 of the rear side of the bottom garment main body 100.

The first to seventh rings may be detachable and attachable. The first to seventh rings may be coupled to the bottom garment main body 100 through hooks, Velcro tapes, and buttons. Through this, the positions of the first to seventh rings can be changed. Through this, the position at which the correction band 200 is being bent can be changed, so that it is possible to deform the pelvis and correct X-shaped legs. That is, it can be corrected by attaching the first to seventh rings to the area in need of correction.

The first part 211 and the third part 213 of the first correction band 210 and the first part 221 and the third part 223 of the second correction band 220 may be formed of an inelastic material. In this case, the inelastic material may include nylon, but is not limited thereto. The second part 212 of the first correction band 210 and the second part 222 of the second correction band 220 may be formed of an elastic material. In this case, the elastic material may include spandex. However, this is not limited, and the first part 211 of the first correction band 210, the first part 221 of the third part 213, the second correction band 220, and the third part 223 may be formed by any one among a stretchable material, a non-stretchable material, and a blend of stretchable and non-stretchable materials.

The second parts 212 and 222 of the first and second correction bands 210 and 220 are formed of an elastic material and can be deformed to fit the size of the user's foot. Specifically, referring to FIG. 6, the second parts 212 and 222 of the first and second correction bands 210 and 220 may be formed to cover only the user's instep. In addition, the second parts 212 and 222 of the first and second correction bands 210 and 220 may be formed to cover the user's instep and at least a portion of a portion being connected from the instep to the ankle. Since the first and third parts 211 and 213 of the first correction band 210 and the first and third parts 221 and 223 of the second correction band 220 are formed of an inelastic material, the effect of correction may be increased. However, it is not limited thereto, and the second parts 212 and 222 of the first and second correction bands 210 and 220 may be formed of any one among a stretchable material, a non-stretchable material, and a blend of stretchable and non-stretchable materials.

Hereinafter, a process in which a walking gait is being corrected by the compression garment for correcting lower body shape and walking gait for angular deformity of legs according to the present embodiment will be described.

Referring to FIG. 5, a posture for correct walking may be naturally maintained when a user walks while wearing the correction band 200. Specifically, it is possible to prevent the user's ankle joint from being rotated outwardly by the third parts 213 and 223 of the first and second correction bands 210 and 220. That is, the angle of the user's ankle joint may be maintained at an ideal angle for a straight walking gait.

In addition, due to the first and third bent portions 213-1 and 223-1 of the first and second correction bands 210 and 220 disposed on an outer side near the user's knee, the correction band 200 may apply pressure in a direction from an outer side to an inner side of the knee joint. Through this, it is possible to prevent the user's knee joint from being rotated outward. That is, the angle of the user's knee joint may be maintained at an ideal angle for a straight walking gait.

In addition, due to a portion being disposed on a rear surface of the bottom garment main body 100, in which the first and second correction bands 210 and 220 are being crossed each other, pressure can be applied in a way that the user's waist muscles are stretched. Through this, the facet joint of the user's spine can maintain the angle for the correct posture for correction. Specifically, it is possible to maintain an angle at which the upper body is slightly bent forward. Through this, the center of gravity of the body acts forward when walking, so that correct walking gait can be induced. That is, if the user walks while wearing the correction band 200, the user's weight can be distributed to induce a correct walking gait for correction of a walking gait.

Through the compression garment for correcting lower body shape and walking gait for angular deformity of legs according to the present embodiment, it is possible to prevent rotational deformation of the pelvis and knee joints, which are the central axes of walking. In addition, incorrect walking gait such as nasolabial walking gait can be corrected through angular correction of rotational deformation of the pelvis or ankle joint. Through this, it is possible to prevent the occurrence of musculoskeletal diseases such as spinal diseases and knees caused by incorrect walking gait.

The embodiments of the present invention have been described above with reference to the accompanying drawings, but a person skilled in the art to which the present invention belongs may understand that the present invention can be implemented in other specific forms without changing the technical spirit or essential features. Therefore, it should be understood that the embodiments described above are illustrative and non-limiting in all respects.

What is claimed is:

1. A compression garment for correcting a lower body shape and a walking gait for an angular deformity of the legs comprising:
a bottom garment main body; and
a correction band disposed on the bottom garment main body,
wherein the correction band includes a first correction band disposed in a first area of the bottom garment main body and a second correction band disposed in a second area of the bottom garment main body,
wherein the first correction band includes a first part disposed above the first area, a second part disposed below the first area, and a third part connecting the first part of the first correction band and the second part of the first correction band,
  wherein the second correction band includes a first part disposed above the second area, a second part disposed below the second area, and a third part connecting the first part of the second correction band and the second part of the second correction band,
  wherein the first correction band includes a connecting member disposed on the first part of the first correction band and including a hole,
  wherein the first part of the second correction band is inserted into the hole of the connecting member of the first correction band and coupled by means of a belt fastener,
  wherein the first part and the third part of the first correction band and the first part and the third part of the second correction band are formed of an inelastic material, and
  wherein the second part of the first correction band and the second part of the second correction band are formed of an elastic material.

2. The compression garment for correcting a lower body shape and a walking gait for an angular deformity of the legs according to claim 1, wherein the third part of the first correction band includes a bent portion formed in a portion being connected from the front side of the first area of the bottom garment main body to the rear side thereof, and
  wherein the third part of the second correction band includes a bent portion being formed in a portion being connected from a front side of the second area of the bottom garment main body to a rear side thereof.

3. The compression garment for correcting a lower body shape and a walking gait for an angular deformity of the legs according to claim 2,
  wherein the bent portion of the third part of the first correction band includes a first bent portion disposed on an outer side surface of the first area of the bottom garment main body, and a second bent portion spaced apart from the first bent portion and disposed on an inner side surface of the first area of the bottom garment main body, and
  wherein the bent portion of the third part of the second correction band includes a third bent portion disposed on an outer side surface of the second area of the bottom garment main body, and a fourth bent portion spaced apart from the third bent portion and disposed on an inner side surface of the second area of the bottom garment main body.

4. The compression garment for correcting a lower body shape and a walking gait for an angular deformity of the legs according to claim 3, wherein the first bent portion of the third part of the first correction band is disposed closer to the second part of the first correction band than the first part of the first correction band, and the second bent portion of the third part of the first correction band is disposed closer to the first part of the first correction band than the second part of the first correction band, and
  wherein the third bent portion of the third part of the second correction band is disposed closer to the second part of the second correction band than the first part of the second correction band, and the fourth bent portion of the third part of the second correction band is disposed closer to the first part of the second correction band than the second part of the first correction band.

5. The compression garment for correcting a lower body shape and a walking gait for an angular deformity of the legs according to claim 4, wherein the first area of the bottom garment main body includes first and second rings formed at positions corresponding to the first and second bent portions of the first correction band and including holes,
  wherein the second area of the bottom garment main body includes third and fourth rings formed at positions corresponding to the third and fourth bent portions of the second correction band and including holes,
  wherein each of the first and second bent portions of the first correction band is respectively inserted into the first and second rings of the first area of the bottom garment main body, and
  wherein each of the third and fourth bent portions of the second correction band is respectively inserted into the third and fourth rings of the second area of the bottom garment main body.

6. The compression garment for correcting a lower body shape and a walking gait for an angular deformity of the legs according to claim 5, wherein the first to fourth rings are detachable from and attachable to the bottom garment main body.

7. The compression garment for correcting a lower body shape and a walking gait for an angular deformity of the legs according to claim 2, wherein the first area of the bottom garment main body includes a ring formed at a position corresponding to the bent portion of the third part of the first correction band, and
  wherein the second area of the bottom garment main body includes a ring formed at a position corresponding to the bent portion of the third part of the second correction band.

8. The compression garment for correcting a lower body shape and a walking gait for an angular deformity of the legs according to claim 1, wherein the bottom garment main body includes a first taping member continuously wound in a first direction from an upper portion of the first area to a lower portion of the first area, and a second taping member continuously wound in a second direction from an upper portion of the first area to a lower portion of the first area, and
  wherein the first direction and the second direction are opposite directions.

9. The compression garment for correcting a lower body shape and a walking gait for an angular deformity of the legs according to claim 8, wherein the density of the first taping member is different from the density of the second taping member.

10. The compression garment for correcting a lower body shape and a walking gait for an angular deformity of the legs according to claim 9, wherein a density of the first taping member is greater than a density of the second taping member.

11. The compression garment for correcting a lower body shape and a walking gait for an angular deformity of the legs according to claim 1, wherein the first and second correction bands are detachable from and attachable to the bottom garment main body.

* * * * *